US005777187A

United States Patent [19]

Knifton et al.

[11] Patent Number: 5,777,187
[45] Date of Patent: Jul. 7, 1998

[54] TWO-STEP PROCESS FOR ALKYLATION OF BENZENE TO FORM LINEAR ALKYLBENZENES

[75] Inventors: John F. Knifton; Prakasa Rao Anantaneni, both of Austin, Tex.

[73] Assignee: Huntsman Petrochemical Corporation, Austin, Tex.

[21] Appl. No.: 662,786

[22] Filed: Jun. 12, 1996

Related U.S. Application Data

[63] Continuation-in-part of Ser. No. 598,692, Feb. 8, 1996.
[51] Int. Cl.$^6$ ........................................ C10C 2/64
[52] U.S. Cl. .................. 585/449; 585/446; 585/447; 585/463; 585/467
[58] Field of Search ........................ 585/446, 447, 585/463, 467, 449; 422/151

[56] References Cited

U.S. PATENT DOCUMENTS

| | | |
|---|---|---|
| 3,436,432 | 4/1969 | Mische . |
| 3,551,510 | 12/1970 | Pollitzer et al. . |
| 3,594,331 | 7/1971 | Elliott, Jr. . |
| 3,630,965 | 12/1971 | Voorhies, Jr. et al. . |
| 3,702,312 | 11/1972 | Wilson . |
| 3,763,260 | 10/1973 | Pollitzer . |
| 3,849,340 | 11/1974 | Pollitzer . |
| 3,873,632 | 3/1975 | Pollitzer . |
| 3,933,983 | 1/1976 | Elliott, Jr. . |
| 4,232,177 | 11/1980 | Smith, Jr. . |
| 4,283,573 | 8/1981 | Young . |
| 4,301,317 | 11/1981 | Young ........................... 585/455 |
| 4,307,254 | 12/1981 | Smith, Jr. . |
| 4,849,569 | 7/1989 | Smith, Jr. . |
| 4,891,465 | 1/1990 | Tanguchi et al. ................ 585/463 |
| 4,918,244 | 4/1990 | Nelson et al. . |
| 4,950,834 | 8/1990 | Arganbright et al. . |
| 4,973,780 | 11/1990 | Johnson et al. ................. 585/467 |
| 4,978,807 | 12/1990 | Smith, Jr. . |
| 5,034,564 | 7/1991 | Kocal ............................ 585/467 |
| 5,043,506 | 8/1991 | Crossland . |
| 5,055,627 | 10/1991 | Smith, Jr. et al. . |
| 5,082,990 | 1/1992 | Hsieh et al. .................... 585/467 |
| 5,107,027 | 4/1992 | Knifton et al. . |
| 5,120,403 | 6/1992 | Smith, Jr. . |
| 5,146,026 | 9/1992 | Tejero et al. ................... 585/467 |
| 5,169,992 | 12/1992 | Knifton . |
| 5,171,896 | 12/1992 | Knifton et al. . |
| 5,175,135 | 12/1992 | Lee et al. . |
| 5,176,883 | 1/1993 | Smith, Jr. et al. . |
| 5,177,280 | 1/1993 | Juguin et al. . |
| 5,196,574 | 3/1993 | Kocal ............................ 562/94 |
| 5,198,595 | 3/1993 | Lee et al. . |
| 5,204,064 | 4/1993 | Smith, Jr. . |
| 5,221,441 | 6/1993 | Smith, Jr. . |
| 5,233,111 | 8/1993 | Notte et al. . |
| 5,243,115 | 9/1993 | Smith, Jr. et al. . |
| 5,243,116 | 9/1993 | Lee et al. . |
| 5,262,576 | 11/1993 | Smith, Jr. . |
| 5,273,644 | 12/1993 | Wegerer ........................ 208/66 |
| 5,304,681 | 4/1994 | Knifton et al. . |
| 5,313,005 | 5/1994 | Smith, Jr. et al. . |
| 5,334,793 | 8/1994 | Kocal . |
| 5,344,997 | 9/1994 | Kocal ............................ 568/628 |
| 5,345,006 | 9/1994 | Smith, Jr. . |
| 5,368,691 | 11/1994 | Asselineau et al. . |
| 5,446,223 | 8/1995 | Smith, Jr. . |

FOREIGN PATENT DOCUMENTS

| | | |
|---|---|---|
| 0 160 144 | 11/1985 | European Pat. Off. . |
| 0 160 145 | 11/1985 | European Pat. Off. . |
| 0 288 582 | 11/1988 | European Pat. Off. . |
| 0 353 813 | 2/1990 | European Pat. Off. . |
| 0 466 558A1 | 1/1992 | European Pat. Off. . |
| 0 692 307 | 1/1996 | European Pat. Off. . |
| WO 93/00317 | 1/1993 | WIPO . |

OTHER PUBLICATIONS

Almeida, J. L. G. de, M. Dufaux, Y. B. Taarit and C. Naccache, Effect of pore size and aluminum content on the production of linear alkylbenzenes over HY, H–ZSM–5 and H–ZSM–12 zeolites: alkylation of benzene with 1–dodecene, *Applied Catalysis A: General* 114: 141–159, 1994.

Almeida, J. L. G. de, M. Dufaux, Y. B. Taarit and C. Naccache, Linear alkylbenzene, *JAOCS* 71 (7): 675–694, 1994.

Cohen, L., R. Vergara, A. Moreno and J. L. Berna, Influence of 2–phenyl alkane and tetralin content on solubility and viscosity of linear alkylbenzene sulfonate, *JAOCS* 72 (1): 115–122, 1995.

Venuto, P. B., L. A. Hamilton, P. S. Landis and J. J. Wise, Organic reactions catalyzed by crystalline aluminosilicatesI. alkylation reactions, *Journal of catalysis* 4: 81–98, 1966.

Hauan et al., "Why methyl tert–butyl ether production by reactive distilliation may yield multiple solutions," *Ind. Eng. Chem. res.*, 34–987–991 (1995).

Matouq et al., "Combined process for production of methyl tert–butyl ether from tert–butyl alcohol and methanol," *J. chem. Engl. JPN*, 27(3):302–306 (1994).

*Primary Examiner*—Helane Myers
*Attorney, Agent, or Firm*—Jones, O'Keefe & Egan

[57] ABSTRACT

This invention is directed to a fluorine-containing mordenite catalyst and use thereof in the manufacture of linear alkylbenzene (LAB) by alkylation of benzene with an olefin. The olefin may have from about 10 to 14 carbons. The fluorine-containing mordenite is prepared typically by treatment with an aqueous hydrogen fluoride solution. The benzene alkylation may be conducted using reactive distillation. Yield and bromine index of the LAB may be improved by further alkylation using a fluorine containing clay catalyst such as montmorillonite clay.

22 Claims, 2 Drawing Sheets

TWO-STEP PROCESS FOR ALKYLATION OF BENZENE TO FORM LINEAR ALKYLBENZENES

This application is a continuation-in-part of patent application Ser. No. 08/598,692, filed Feb. 8, 1996.

BACKGROUND OF THE INVENTION

This invention generally relates to the alkylation of benzene with olefins using mordenite catalysts.

Linear alkyl benzenes (LAB's) having long chains (typically 10–14 carbons) are commonly used, commercial products. LAB's are commonly sulfonated to thereby produce surfactants.

Typically, LAB's are manufactured commercially using classic Friedal-Crafts chemistry, employing catalysts such as aluminum chloride, or using strong acid catalysts such as hydrogen fluoride, for example, to alkylate benzene with olefins. While such methods produce high conversions, the selectivity to the 2-phenyl isomer is low, generally being about 30% or less. LAB's with a high percentage of the 2-phenyl isomer are highly desired because such compounds when sulfonated have long "tails" which provide enhanced solubility and detergent properties.

SUMMARY OF THE INVENTION

It has now been recognized that a need exists for a method of LAB production having high substrate olefin conversion, high selectivity to 2-phenyl isomer LAB, and employing a catalyst having long lifetimes and easy handling. This invention provides a solution to one or more of the problems and disadvantages described above.

This invention, in one broad respect, is a process useful for the production of monoalkylated benzene, comprising the steps of: (a) contacting benzene with an olefin containing from about 5 to about 30 carbons in the presence of fluorine-containing mordenite under conditions such that linear monoalkylated benzene is formed; and (b) contacting the effluent from step (a) with benzene in the presence of a fluorine-containing clay catalyst such that the product of step (b) has a bromine number less than the bromine number of the product of step (a).

In a second broad respect, this invention is a process useful for the production of monoalkylated benzene, comprising the steps of: introducing a feed comprising olefin having about 5 to about 30 carbons and benzene into a fluorine-containing mordenite catalyst bed under conditions such that monoalkylated benzene is produced, allowing benzene, olefin, and monoalkylated benzene to descend (fall) into a reboiler from the catalyst bed, removing monoalkylated benzene from the reboiler, heating the contents of the reboiler such that benzene refluxes to further contact the fluorine-containing mordenite, and contacting the monoalkylated benzene removed from the reboiler with benzene in the presence of a fluorine-containing clay catalyst such that the bromine number of the monoalkylated benzene removed from the reboiler is reduced.

In another broad aspect, this invention relates to mordenite useful for alkylating benzene with olefin having a silica to alumina molar ratio of about 10:1 to about 100:1; wherein the mordenite has been treated with an aqueous hydrogen fluoride solution such that the mordenite contains from about 0.1 to about 4 percent fluorine by weight.

In another broad respect, this invention is a method useful for the preparation of fluorine-containing mordenite, comprising contacting a mordenite having a silica to alumina molar ratio in a range from 10:1 to about 100:1 with an aqueous hydrogen fluoride solution having a concentration of hydrogen fluoride in the range of from about 0.1 to about 10 percent by weight such that the mordenite containing fluorine is produced, collecting the fluorine-containing mordenite by filtration, and drying.

The fluorine treated mordenite catalyst advantageously produces high selectivities to the 2-phenyl isomer in the preparation of LAB, generally producing selectivities of about 70 percent or more. Also, the fluorine treated mordenite enjoys a long lifetime, preferably experiencing only a 25 percent or less decrease in activity after 400 hours on stream. A process operated in accordance with the apparatus depicted in FIGS. 1 and 2 has the advantage that rising benzene from the reboiler continuously cleans the catalyst to thereby increase lifetime of the catalyst. In addition, this invention advantageously produces only low amounts of dialkylated benzene, which is not particularly as useful for detergent manufacture, as well as only low amounts of tetralian derivatives.

In addition, the two-step process wherein a fluorine-containing clay catalyst is used in the second alkylation step leads to increased concentration of alkylated products, as well as decreased bromine number of the resulting product relative to the bromine number of the alkylated product using mordenite in a one-step reaction.

Certain terms and phrases have the following meanings as used herein.

"Meq/g" means milliequivalents of titratable acid per gram of catalyst, which is a unit used to describe acidity of the catalysts. Acidity is generally determined by titration with a base, as by adding excessive base, such as sodium hydroxide, to the catalyst and then back titrating the catalyst. "Conv." and "Conversion" mean the mole percentage of a given reactant converted to product. Generally, olefin conversion is about 95 percent or more in the practice of this invention. "Sel." and "Selectivity" mean the mole percentage of a particular component in the product. Generally, selectivity to the 2-phenyl isomer is about 70 or more in the practice of this invention. "Bromine number" means grams of bromine consumed per 100 g of sample and is determined by titrating with bromide/bromate solution.

The mordenite catalyst of the present invention is useful as a catalyst in the production of LAB's in accordance with the process of manufacturing LAB's of this invention. LAB is useful as starting material to produce sulfonated LAB, which itself is useful as a surfactant.

DETAILED DESCRIPTION OF THE PREFERRED EMBODIMENTS

Catalyst Preparation and Properties

Figure 1:
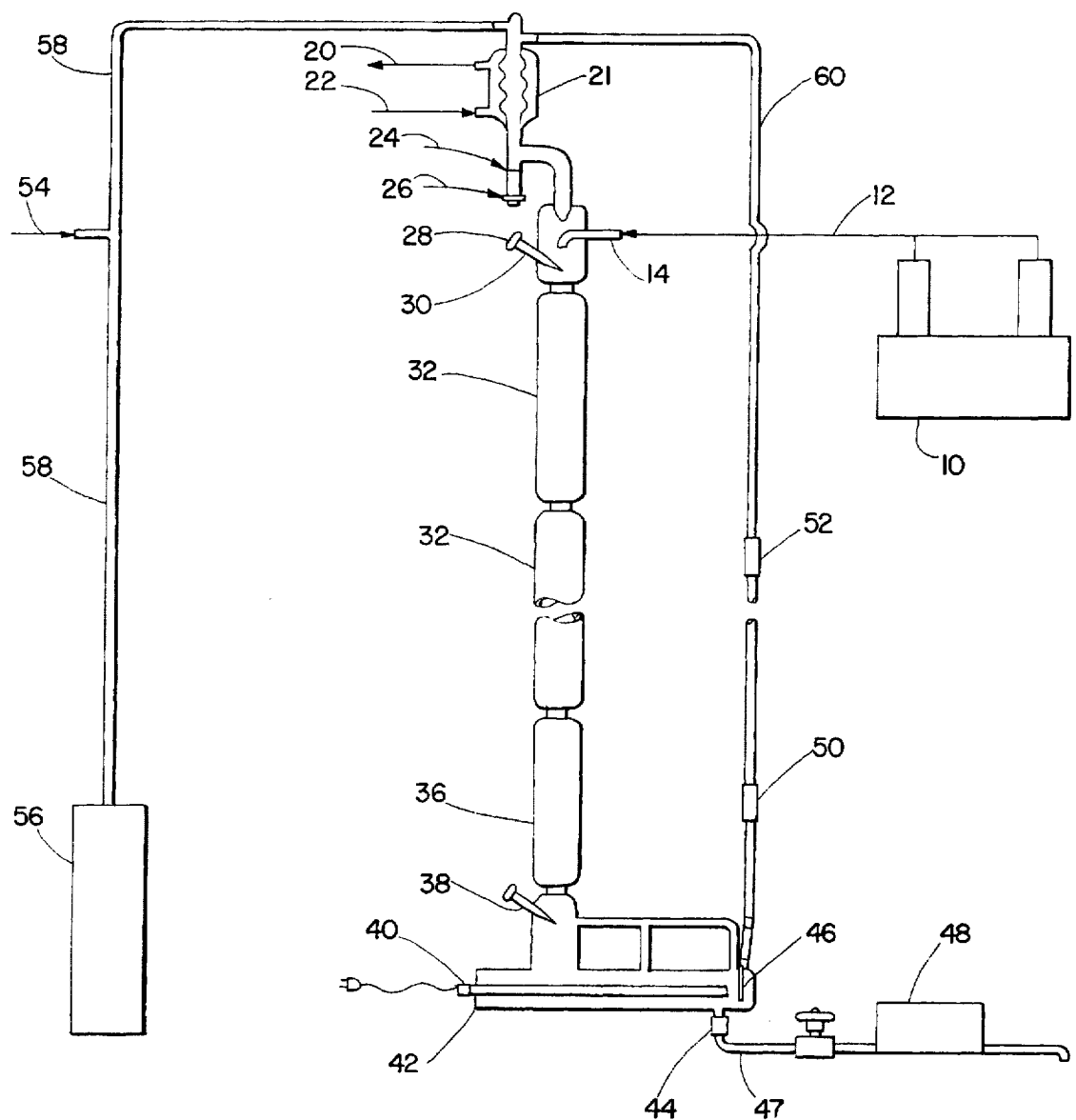
FIG. 1 shows a representation of a first continuous reactive distillation column employed in the practice of this invention.

The first catalyst employed in the practice of this invention is a fluorine-containing mordenite. Mordenite is a type of zeolite. The catalyst of this invention is prepared from hydrogen mordenite (typically having 0.1 percent or less of sodium) having a silica-alumina molar ratio of from about 10:1 to about 100:1. More typically, the starting mordenite has a silica/alumina molar ratio of from about 10:1 to about 50:1. The starting hydrogen mordenite, which is commonly available commercially, is treated with an aqueous solution of hydrogen fluoride ("HF") to produce the active, long-life and highly selective catalyst of the invention. In the course of such HF treatment, as well as during subsequent calcination of said HF-treated mordenite, the silica/alumina molar ratio typically increases. The finished catalysts of this invention show a fluorine content of from about 0.1 to about 4 percent by weight, more typically about 1 percent.

While not wishing to be bound by theory, it is believed that the HF reacts with sites where —Si—O—Al' linkages occur such that the linkage is broken with fluorine becoming bonded to the Al such that —Si—OH and F—Al— groups form. This is believed to decrease the total Bronsted acid sites and increase the strength of the remaining acid sites in the mordenite and is believed to stabilize the acidity of the mordenite such that the mechanisms which degrade performance during LAB production, such as coke build-up, are retarded.

The aqueous solution used to treat the mordenite may contain a range of HF concentrations. Generally, the HF concentration is a minimum of about 0.1 percent by weight. Below such minimum concentration, the effect of the fluorine treatment significantly decreases, resulting in the undesirable need for repeated treatments. Generally, the HF concentration on the upper end is about 10 percent by weight or less. Above a concentration of about 10 percent by weight, the HF is so concentrated that it is difficult to prevent HF from destroying the crystallinity of the mordenite, thereby detrimentally affecting its efficacy as a catalyst for LAB production.

The aqueous HF solution may be prepared by diluting commercially available 48% HF solutions to the desired concentration. Alternatively, HF can be sparged into water to provide an aqueous HF solution.

Typically, the treatment is carried out by adding mordenite powder or pellets to a stirred aqueous HF solution at a temperature of from about 0° C. to about 50° C. The stirring and contacting is continued for a time sufficient to achieve the desired level of fluorine in the mordenite. This time may vary depending on factors such as HF concentration, amount of HF solution relative to the amount of mordenite being treated, speed of agitation employed, and temperature. After treatment, the mordenite can be recovered by filtration, and then dried. It is also possible to impregnate the mordenite to incipient wetness with a given HF solution, as well as to treat the mordenite with gaseous hydrogen fluoride. Preferably said fluoride-treated mordenite would be calcined in air prior to use in alkylation service. The preferred calcination temperature would be in the range from about 400° C. to about 600° C. Alternative mordenite fluorinating agents to hydrofluoric acid and hydrogen fluoride include ammonium fluoride, fluorided silicon compounds and fluorided hydrocarbons.

The HF-treated mordenite of this invention generally has about 0.1 percent by weight or more of fluorine based on the total weight of the mordenite. Typically, the fluorine-containing mordenite contains about 4 percent by weight or less fluorine. The fluorine-containing mordenite most typically contains about 1 percent by weight of fluorine.

The mordenite can be used in the practice of this invention as a powder, in pellet form, as granules, or as extrudates. The mordenite can be formed into pellets or extrudates using binders well known to those of skill in the art, such as alumina, silica or mixtures thereof.

The fluorine-containing clay catalyst used in the process of this invention may be prepared from a variety of clays, particularly the class of smeltite clays. One representative example of such clays is montmorillonite. Such clays are commonly available commercially in neutral, basic, and acidic forms, having a surface area greater than about 30 $m^2/g$ and a moisture content of zero to about 20 wt %. The starting clay material is treated with an aqueous solution of HF as described hereinabove, as well as is described in U.S. Pat. No. 5,157,161. The finished clay catalysts have a fluorine content of from about 0.1 percent to about 10 percent by weight, typically from about 0.1 to about 4 percent by weight, more typically about 0.5 percent. Optionally, said modified clays may be calcined, typically at temperatures from about 100° C. to about 600° C.

The fluorine-containing clay may be used as a powder, in pellet form, as granules, or as extrudates. The clay can be formed into pellets or extrudates using binders well known to those of skill in the art, such as alumina, silica, or mixtures thereof.

Reactants for LAB Production

In the practice of this invention, benzene is alkylated with olefin to form LAB. These reactants can be handled and purified as is generally performed by those of skill in the art. In this regard, it is preferred that the reactants are water and alcohol free. The olefins employed in the practice of this invention have from about 5 to about 30 carbons, preferably from about 10 to about 14 carbons, such as is available commercially or produced as dehydrogenated paraffin feed stocks. It is preferred that the olefin be monounsaturated. It is most preferred that the olefin be an alpha-olefin containing a terminal ethylenic unit.

Commonly, said olefins would be available in a paraffinic media of the same carbon range. Olefins in the 10 to 14 carbon number range would typically be available from $C_{10}$ to $C_{14}$ paraffin dehydrogenation in a $C_{10}$ to $C_{14}$ paraffin mixture having an olefin content of 5 to 20%. Often, the olefin content of said olefin-paraffin mixture would be 8 to 10 weight %.

The 2-phenyl isomer of the LAB produced in accordance with this invention is of formula:

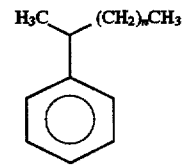

wherein n is from about 2 to about 17 and preferably from about 7 to about 11.

Process Conditions, Procedures, and Apparatus

The first step of the process of this invention can be carried out using the continuous reactive distillation column depicted in FIG. 1. In FIG. 1, a feed mixture of benzene and olefin, generally at a benzene-to-olefin molar ratio range of about 1:1 to 100:1 flows from feed pump 10 to feed inlet 14 via line 12. The feed mixture falls to packed mordenite catalyst bed 32 where alkylation in the presence of the fluorine-containing mordenite occurs. Alternatively, while not depicted in FIG. 1, the benzene and olefin can be introduced separately into the bed with mixing occurring in the bed, or the reactants can be mixed via an in-line mixer prior to introducing the reactants into the catalyst bed, or the reactants can be injected separately above the bed with mixing affected by use of standard packing above the bed, or the reactants can be sparged into the chamber above the bed. The catalyst bed 32 depicted in FIG. 1 for laboratory scale may be made of two lengths of 1.1 inch internal diameter tubing, the lengths being 9.5 inches and 22 inches. In the catalyst bed 32, the falling feed mixture also contacts rising vapors of unreacted benzene which has been heated to reflux in reboiler 42 by heater 40. Such rising vapors pass over thermocouple 38 which monitors temperature to provide feedback to heater 40. The rising vapors of benzene and/or olefin also pass through standard packing 36 (e.g., 7.5 inches of goodloe packing). The rising vapors heat thermocouple 30 which connects to bottoms temperature controller 28 which activates heater 40 when temperature drops below a set level.

Prior to startup, the system may be flushed with nitrogen which enters via line 54 and which flows through line 58. After startup, a nitrogen blanket is maintained over the system. Also prior to startup and during nitrogen flush, it may be desirable to heat catalyst bed 32 so as to drive off water from the fluorine-containing mordenite.

Residual water from the feed mixture or which otherwise enters the system is collected in water trap 24 upon being liquified at condenser 21 (along with benzene vapor). If the feed is very dry (free of water) the water trap 24 may not be needed. Removing water leads to longer catalyst lifetime. Hence, the water trap 24 is optional. The same applies to FIG. 2. Condenser 21 is cooled via coolant such as water entering condenser 21 via port 22 and exiting via port 20. As needed, water in water trap 24 may be drained by opening drain valve 26.

As needed, when LAB content in reboiler 42 rises to a desired level, the bottoms LAB product may be removed from the system via line 47, using either gravity or bottoms pump 48 to withdraw the product. When product is so withdrawn, valve 44 is opened.

In FIG. 1, dip tube 46, which is optional, is employed to slightly increase the pressure in reboiler 42 to thereby raise the boiling point of benzene a degree or two. Likewise, a pressure generator 56 may be optionally employed to raise the pressure of the system. Other standard pressure increasing devices can be employed. Pressure can thus be increased in the system such that the boiling point of benzene increases up to about 200° C.

In FIG. 1, control mechanisms for heat shutoff 50 and pump shutoff 52 are depicted which serve to shut off heat and pump if the liquids level in the system rises to such levels. These control mechanisms are optional and may be included so that the catalyst bed does not come into contact with the bottoms of the reboiler.

Figure 2:
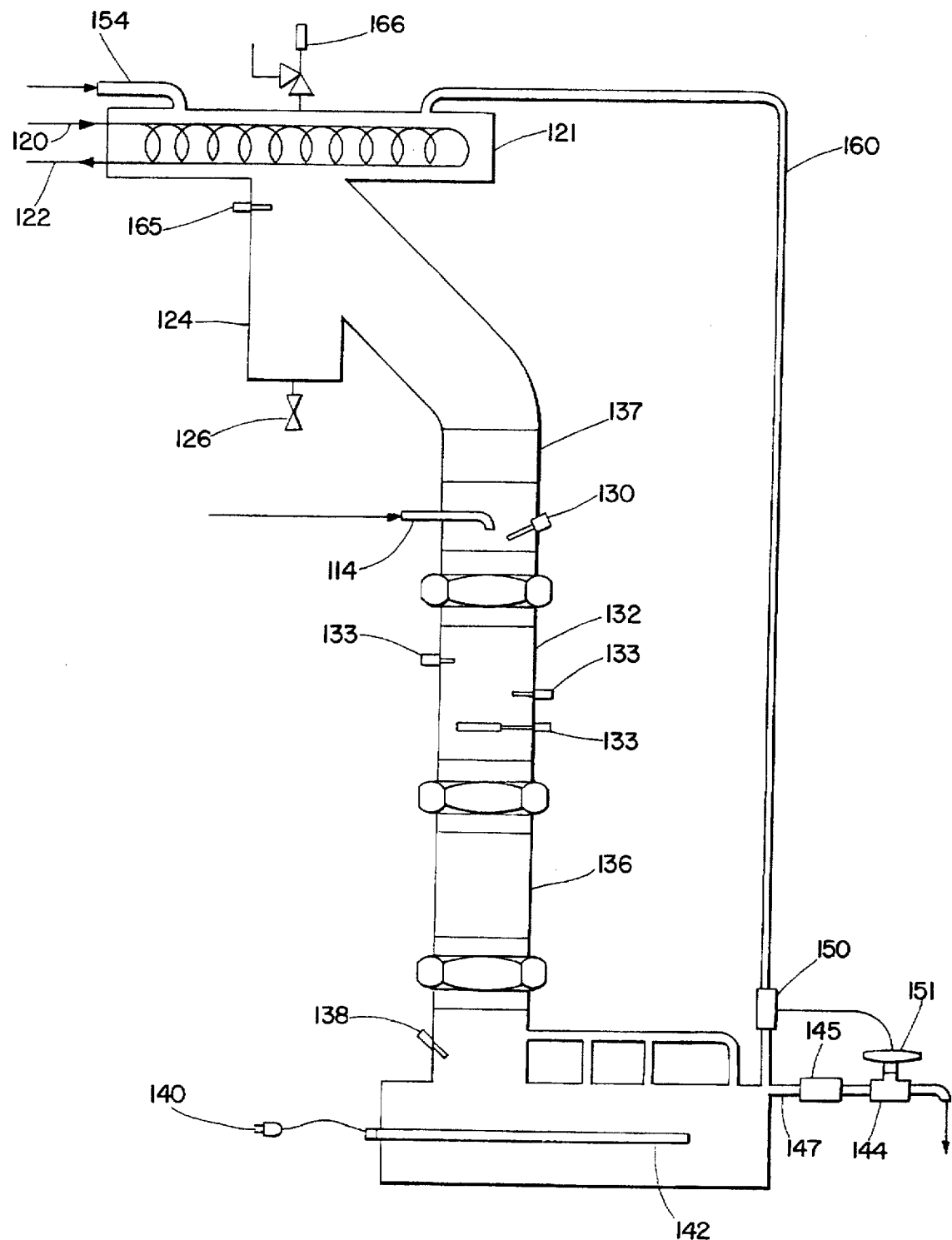
FIG. 2 shows a representation of a second continuous reactive distillation column employed in the practice of this invention.

In the practice of this invention in the alkylation of benzene, a wide variety of process conditions can be employed. In this regard, the temperature in the catalyst bed may vary depending on reactants, rate of introduction into the catalyst bed, size of the bed, and so forth. Generally, the bed is maintained at the reflux temperature of benzene depending on pressure. Typically, the temperature of the catalyst bed is above about 70° C., and most likely about 78° C. or more in order to have reasonable reaction rates, and about 200° C. or less to avoid degradation of reactants and products and to avoid deactivation of the catalyst by coke build-up. Preferably, the temperature is in the range from about 80° C. to about 140° C. The process may be operated at a variety of pressures during the contacting step, with pressures of about atmospheric most typically being employed. When the process is operated using a system as depicted in FIGS. 1 and 2, the reboiler temperature is maintained such that benzene and olefin vaporize, the temperature varying depending on olefin, and generally being from about 80° C. to about 250° C. for olefins having 10 to 14 carbons. The composition of the reboiler will vary over time, but is generally set initially to have a benzene olefin ratio of about 5:1, with this ratio being maintained during the practice of this invention. The rate of introduction of feed into the catalyst bed may vary, and is generally at a liquid hourly space velocity ("LHSV") of about 0.05 $hr^{-1}$ to about 10 $hr^{-1}$, more typically from about 0.05 $hr^{-1}$ to about 1 $hr^{-1}$. The mole ratio of benzene to olefin introduced into the catalyst bed is generally from about 1:1 to about 100:1. In commercial benzene alkylation operations, it is common to run at mole ratios of from about 2:1 to about 20:1, which can suitably be employed in the practice of this invention, and to charge said olefins as an olefin-paraffin mixture comprising 5% to 20% olefin content. Said olefin-paraffin mixtures are normally generated commercially through dehydrogenation of the corresponding paraffin starting material over a noble metal catalyst.

Another continuous reactive distillation apparatus is depicted in FIG. 2. In FIG. 2, the feed mixture enters the reactor via feed inlet 114. The feed mixture falls through the column into catalyst bed 132, wherein alkylation to form LAB occurs. A thermowell 133 monitors the temperature of said catalyst bed 132. The catalyst bed 132 may be optionally heated externally and is contained within 1¼ inch stainless steel tubing. Goodloe packing is positioned at packing 136 and 137. LAB product, as well as unreacted benzene and olefin, fall through packing 136 into reboiler 142. In reboiler 142, electric heater 140 heats the contents of reboiler 142 such that heated vapors of benzene and olefin rise from the reboiler 142 to at least reach catalyst bed 132. As needed, the bottoms LAB product may be removed from reboiler 142 by opening bottoms valve 144 after passing through line 147 and filter 145. Residual water from the feed mixture, or which otherwise enters the system, may be condensed at condenser 121 which is cooled with coolant via inlet line 122 and exit line 120. The condensed water falls to water trap 124, which can be drained as needed by opening drain valve 126. Temperature in the system is monitored via thermocouples 138, 130, and 165. The system includes pressure release valve 166. A nitrogen blanket over the system is maintained by introduction of nitrogen gas via inlet line 154. Level control activator 150 activates bottoms level control valve 151 to open when the liquids level in the reboiler rises to the level control activator 150.

While the systems depicted in FIG. 1 and FIG. 2 show single catalyst bed systems, it may be appreciated that multi-catalyst bed reactors are within the scope of this invention, as well as multiple ports for inlet feeds, water traps, product removal lines, and so forth. Moreover, the process may be run in batch mode, or in other continuous processes using plugflow designs, trickle bed designs, and fluidized bed designs.

It is believed that as average molecular weight of olefins increases, particularly when the average number of carbons exceed 14, the selectivity and conversion to LAB, especially LAB with the 2-isomer, may incrementally decrease.

The product of the alkylation using HF-treated mordenite may be sent to a second, finishing catalyst bed to improve LAB yield and quality. An example of such a second catalyst is HF-treated clay such as montmorillonite clay having about 0.5% fluoride. Such a catalyst may also serve to lower the bromine number below about 0.1, depending on conditions.

In the practice of this invention, the effluent from the alkylation using HF-treated mordenite is mixed with additional benzene and the mixture heated in the presence of the fluorine-containing clay catalyst as by passing the mixture through the clay catalyst bed at benzene reflux temperatures. The amount of added benzene may vary and is generally added in amounts of about 5 to about 10 moles benzene per mole of olefin. Higher benzene levels may be used as necessary to limit olefin dimerization. Reaction times and contact times may vary depending on the extent of conversion of olefin on the hydrogen fluoride-treated mordenite. Also, LHSV, temperature, and pressure may also be varied under some circumstances to influence the product make-up.

This second alkylation step may be conducted batch-wise, or continuously using, for example, a plug flow, continuous reactor configuration. The temperatures and pressured in this second step are substantially the same as described above for the first alkylation step using the mordenite catalyst. The amount of benzene added may vary, and is generally in the benzene-to-olefin molar ratio range of about 1:1 to about 1000:1. Reaction times and contact times may vary depending on desired extent of reaction, amount of catalyst, temperature and other parameters. Typically, in continuous operation, the clay catalyst bed is maintained in the temperature range of 70° C. to 200° C. and the unit operated at pressures of zero to about 1000 psi. Liquid hourly space velocities of about 0.05 hr$^{-1}$ to about 10 hu$^{-1}$ are employed.

Depending on the initial bromine number, the bromine number of the product of the first reaction may be reduced over 1 unit after the second step, using the clay catalyst. The bromine number is typically reduced to a value of less than about 0.1, and may be reduced to less than about 0.005. The second step may also improve the yield to provide a higher total alkylate concentration. Generally, the second step not only improves the bromine number of alkylate, but also increases the alkylate yield by 0.10–1.00%, depending upon the olefin conversion in the first step.

The starting material, which may contain varied levels of olefins, is typically converted by greater than about 90% in the first stage. Below that level, the catalyst needs regeneration. The conversion in the first state can go as high as about 99%, and reaches about 99.9% after the second treatment.

The following examples are illustrative of the present invention and are not intended to be construed as limiting the scope of the invention or the claims. Unless otherwise indicated, all percentages are by weight. In the examples, all reactants were commercial grades and used as received. The apparatus depicted in FIG. 1 was employed for examples 2–4. The apparatus depicted in FIG. 2 was used for example 5.

It may be noted that example 2 illustrates LAB production from paraffin dehydrogenate using the fluoride-treated mordenite catalyst of example B, where good catalyst life (250+hrs) is achieved without catalyst regeneration, while maintaining a 2-phenyl LAB selectivity of >70% and high LAB productivity without significant loss of fluoride. Comparative example 1, on the other hand, using untreated mordenite, with no fluoride added, shows a rapid decline in LAB production. In addition, examples 3 and 4 illustrate LAB production using a 5:1 molar benzene/$C_{10}$–$C_{14}$ olefin feed mix and the fluoride-treated mordenite catalysts of Example B when operating at different LHSV's in the range of 0.2–0.4 hr$^{-1}$. Catalyst life may exceed 500 hours. Example 5 illustrates LAB production with the fluoride-treated mordenite catalyst where the alkylation is conducted at higher temperatures and under pressure. Examples 6–8 illustrate the performance of three HF-treated mordenite catalysts with different fluoride loadings. Example 9 shows how virtually no alkylation activity is observed with a highly-fluorinated mordenite.

Example 10 illustrates the further batch alkylation of crude benzene alkylate from Example 4 using a dried, 0.5% fluorided montmorillonite clay catalyst. Typical bromine numbers for the products after this two-step process are 0.1.

Example 11 illustrates the further alkylation of crude benzene alkylate after stripping to remove benzene plus most of the $C_{10}$–$C_{14}$ paraffin, using the same fluorided montmorillonite clay catalyst, again in a batch mode. The bromine number of the alkylate product was <0.01.

Example 12 shows the use of a plug-flow, continuous reactor configuration and the same fluorided montmorillonite clay catalyst to achieve further alkylation and provide product with a bromine number of 0.02. After stripping, the alkylate purity is 98% and the 2-phenyl isomer content is 76%.

EXAMPLE A

This example illustrates the preparation of a hydrogen fluoride-modified mordenite.

To 30 g of acidified mordenite (LZM-8, SiO$_2$/Al$_2$O$_3$ ratio 17; Na$_2$O wt % 0.02, surface area 517 m$^2$/g, powder, from Union Carbide Corp.) was added 600 ml of 0.4% hydrofluoric acid solution, at room temperature. After 5 hours the solid zeolite was removed by filtration, washed with distilled water, dried at 120° C. overnight, and calcined at 538° C.

EXAMPLE B

The example illustrates the preparation of a hydrogen fluoride-modified mordenite.

To 500 g of acidified, dealuminized, mordenite (CBV-20A from PQ Corp.; SiO$_2$/Al$_2$O$_3$ molar ratio 20; Na$_2$O, 0.02 wt %; surface area 550 m$^2$/g, 1/16" diameter extrudates, that had been calcined at 538° C., overnight) was added a solution of 33 ml of 48% HF solution in 1633 ml of distilled water, the mix was cooled in ice, stirred on a rotary evaporator overnight, then filtered to recover the extruded solids. The extrudates were further washed with distilled water, dried in vacuo at 100° C., and then calcined at 538° C., overnight.

Analyses of the treated mordenite showed:

F: 1.2%

Acidity: 0.49 meq/g

EXAMPLE 1

This example illustrates the preparation of linear alkyl benzenes using a hydrogen fluoride-modified mordenite catalyst.

To a 500 ml flask, fitted with condenser and Dean Stark Trap was added 100 ml of benzene (reagent grade) plus 10 g of hydrogen fluoride-modified mordenite zeolite, prepared by the method of Example A. The mix was refluxed for 15–20 minutes to remove small amounts of moisture, then a combination of benzene (50 ml) plus 1-dodecene (10 g) was injected into the flask and the solution allowed to reflux for 3 hours.

Upon cooling, the modified mordenite catalyst was removed by filtration, the filtrate liquid flashed to remove unreacted benzene, and the bottoms liquid analyzed by gas chromatography.

Typical analytical data are summarized in Table 1.

TABLE 1

| DODECENE CONV. (%) | LAB ISOMER DISTRIBUTION (%) | | | | | HEAVIES (%) | LINEAR LAB (LLAB) (%) |
|---|---|---|---|---|---|---|---|
| | 2-Ph | 3-Ph | 4-Ph | 5-Ph | 6-Ph | | |
| 99.7 | 79.9 | 16.6 | 0.8 | 1.3 | 1.3 | 0.2 | 95.9 |

EXAMPLE 2

This example illustrates the preparation of linear alkylbenzenes from paraffin dehydrogenate using a hydrogen fluoride-treated mordenite catalyst.

In the example, benzene was alkylated with a sample of $C_{10}$–$C_{14}$ paraffin dehydrogenate containing about 8.5% $C_{10}$–$C_{14}$ olefins. Alkylation was conducted in a process unit as shown in FIG. 1.

Alkylation was conducted by first charging 500 ml of a benzene/paraffin dehydrogenate mix (10:1 molar ratio, benzene/$C_{10}$–$C_{14}$ olefin) to the reboiler and 250 cc of the HF-treated mordenite of example B to the 1.1" i.d. reaction zone. The mordenite was held in place using Goodloe packing. The reboiler liquid was then heated to reflux and a benzene plus $C_{10}$–$C_{14}$ paraffin dehydrogenate mix (10:1 molar ratio, benzene/$C_{10}$–$C_{14}$ olefin) continuously introduced into the unit above the catalyst column at the rate of 100 cc/hr. (LHSV=0.4 hr$^{-1}$).

Under steady state, reflux, conditions liquid product was continuously withdrawn from the reboiler and water continuously taken off from the water trap. The crude liquid product was periodically analyzed by gas chromatography. The reboiler temperature was typically in the controlled range of 97°–122° C. The column head temperature variability was 78°–83° C. A summary of the analytical results may be found in Table 2.

After 253 hours on stream, the recovered HF-treated mordenite catalyst showed by analysis:

F: 1.1%
Acidity: 0.29 meq/g
$H_2O$: 0.3%

TABLE 2

| Time on Stream (Hrs) | Sample | Alkylate Conc. (%) | 2-Phenyl Sel. (%) | $C_6H_6$ Conc. (%) |
|---|---|---|---|---|
| 0 | 0 | 1.4 | | 32.3 |
| 2 | 1 | 3.4 | | 19.7 |
| 4 | 2 | 5.8 | 74.9 | 16.6 |
| 6 | 3 | 6.6 | 75.8 | 25.2 |
| 32 | 4 | 7.9 | 80.7 | 27.0 |
| 56 | 5 | 7.8 | 82.7 | 27.0 |
| 69 | 6 | 7.3 | 81.4 | 27.4 |
| 94 | 7 | 6.5 | 82.0 | 27.8 |
| 118 | 8 | 6.0 | 78.4 | 27.7 |
| 142 | 9 | 5.9 | 81.3 | 26.9 |
| 166 | 10 | 5.4 | 81.5 | 27.3 |
| 207 | 11 | 5.3 | 81.3 | 26.1 |
| 229 | 12 | 5.1 | 81.1 | 27.4 |
| 253 | 13 | 4.9 | 81.4 | 28.1 |

Comparative Example 1

This example illustrates the preparation of linear alkyl benzene from paraffin dehydrogenate using an untreated mordenite catalyst.

Following the procedures of Example 2, the alkylation unit was charged with 250 cc of untreated, calcined, mordenite, (the starting mordenite of Example B), and the liquid feed comprised benzene plus $C_{10}$–$C_{14}$ paraffin dehydrogenate mix in a 10:1 molar ratio of benzene/$C_{10}$–$C_{14}$ olefin.

Typical results are summarized in Table 3.

The recovered mordenite showed by analysis:

Acidity: 0.29 meq/g
$H_2O$: 2.1%

TABLE 3

| Time on Stream (Hrs) | Sample | Alkylate Conc. (%) | 2-Phenyl Sel. (%) | $C_6H_6$ Conc. (%) |
|---|---|---|---|---|
| 0 | 0 | | | 11.2 |
| 2 | 1 | 6.50 | | 9.9 |
| 4 | 2 | 7.16 | 73.2 | 17.1 |
| 6 | 3 | 7.09 | 73.1 | 26.4 |
| 22 | 4 | 8.61 | 73.9 | 26.6 |
| 31 | 5 | 10.49 | 67.4 | 15.8 |
| 46 | 6 | 7.39 | 75.0 | 27.7 |
| 70 | 7 | 6.39 | 75.1 | 28.5 |
| 93 | 8 | 6.08 | 73.6 | 23.0 |
| 144 | 9 | 5.21 | 73.6 | 15.8 |
| 157 | 10 | 4.40 | 73.9 | 26.2 |
| 180 | 11 | 3.06 | 69.6 | 27.1 |
| 204 | 12 | 1.32 | | 19.5 |
| 228 | 13 | 1.32 | | 33.3 |

EXAMPLE 3

This example also illustrates the preparation of linear allyl benzene from paraffin dehydrogenate using a hydrogen fluoride-treated mordenite catalyst.

Following the procedures of Example 2, the alkylation unit was charged with 250 cc of the HF-treated mordenite of Example B, and the liquid feed comprised a benzene plus $C_{10}$–$C_{14}$ paraffin dehydrogenate mix in a 5:1 molar ratio of benzene/$C_{10}$–$C_{14}$ olefin, the reboiler temperature was typically in the range of 122°–188° C., the column head temperature 78°–83° C. Typical analytical results are summarized in Table 4.

After 503 hours on stream, the recovered HF-treated mordenite catalyst showed on analysis:

F: 1.0%
Acidity: 0.35 meq/g
$H_2O$: 0.1%

TABLE 4

| Time on Stream (Hrs) | Sample | Alkylate Conc. (%) | 2-Phenyl Sel. (%) | $C_6H_6$ Conc. (%) | Corrected[a] Alkylate Conc. (%) |
|---|---|---|---|---|---|
| 0 | 0 | 1.0 | | 8.9 | 1.1 |
| 2 | 1 | 3.5 | 61.8 | 0.3 | 3.5 |
| 4 | 2 | 7.1 | 72.1 | 0 | 7.1 |
| 6 | 3 | 6.8 | 76.7 | 7.2 | 7.3 |
| 34 | 4 | 8.4 | 79.7 | 14.3 | 9.8 |
| 71 | 5 | 7.2 | 81.8 | 14.6 | 8.5 |
| 96 | 6 | 6.5 | 80.8 | 15.5 | 7.7 |
| 119 | 7 | 6.3 | 80.6 | 15.1 | 7.4 |
| 643 | 8 | 6.0 | 81.0 | 14.3 | 7.0 |
| 168 | 9 | 5.9 | 80.7 | 14.4 | 6.9 |
| 239 | 10 | 5.0 | 78.2 | 8.8 | 5.5 |
| 263 | 11 | 5.3 | 79.2 | 13.5 | 6.2 |
| 288 | 12 | 5.0 | 79.6 | 16.5 | 6.0 |
| 311 | 13 | 5.4 | 79.4 | 4.1 | 5.6 |

TABLE 4-continued

| Time on Stream (Hrs) | Sample | Alkylate Conc. (%) | 2-Phenyl Sel. (%) | $C_6H_6$ Conc. (%) | Corrected[a] Alkylate Conc. (%) |
|---|---|---|---|---|---|
| 335 | 14 | 5.5 | 79.2 | 8.2 | 6.0 |
| 408 | 15 | 4.9 | 79.4 | 13.1 | 5.6 |
| 432 | 16 | 4.7 | 78.8 | 14.4 | 5.5 |
| 456 | 17 | 4.4 | 78.5 | 14.1 | 5.1 |
| 479 | 18[a] | 4.7 | 78.6 | 2.7[b] | 4.8 |
| 488 | 19[b] | 4.9 | 78.5 | 2.4[c] | 5.0 |
| 503 | 20[b] | 5.1 | 78.9 | 0.6[c] | 5.1 |

[a]Corrected for benzene in effluent sample.
[b]Applied pressure 8" $H_2O$
[c]Applied pressure 12" $H_2O$

EXAMPLE 4

This example also illustrates the preparation of linear alkyl benzenes from paraffin dehydrogenate using a hydrogen fluoride-treated mordenite catalyst.

Following the procedures of Example 2, alkylation was conducted in the glassware unit of FIG. 1 complete with catalyst column, reboiler, condenser and controls. To the reaction zone was charged 500 cc of HF-treated mordenite of Example B. The liquid feed comprised a benzene plus $C_{10}$–$C_{14}$ paraffin dehydrogenate mix in a 5:1 molar ratio of benzene /$C_{10}$–$C_{14}$ olefin. The feed rate was 100 cc/hr (LHSV:0.2 hr$^{-1}$).

Under typical steady state, reflux, conditions, with a reboiler temperature range of 131°–205° C. and a head temperature of 76°–83° C., typical results are summarized in Table 5.

EXAMPLE 5

This example illustrates the preparation of linear alkyl benzenes from paraffin dehydrogenate using a hydrogen fluoride-treated mordenite catalyst.

Following the procedures of Example 2, alkylation of benzene with $C_{10}$–$C_{14}$ paraffin dehydrogenate was conducted using the stainless-steel unit of FIG. 2, complete with catalyst column, reboiler, condenser, and controls. About 250 cc or HF-treated mordenite of Example B was charged to the column. The liquid feed comprised benzene plus $C_{10}$–$C_{14}$ paraffin dehydrogenate mix in a 10:1 molar ratio of benzene/$C_{10}$–$C_{14}$ olefin. The LHSV varied from 0.2 to 0.4 hr$^{-1}$.

Alkylation was conducted over a range of column and reboiler temperatures and a range of exit pressures. Typical results are summarized in Table 6.

TABLE 5

| Pressure (Inch $H_2O$) | Reboiler Temp. (°C.) | Time on Stream (Hrs) | Sample | Alkylate Conc. (%) | 2-Phenyl Sel. (%) | $C_6H_6$ Conc. (%) | Corrected[a] Alkylate Conc. (%) |
|---|---|---|---|---|---|---|---|
| 12 | 205 | 2 | 1 | 8.2 | 74.3 | 0.5 | 8.3 |
|  | 193 | 4 | 2 | 9.2 | 75.0 | 0.4 | 9.2 |
|  | 175 | 6 | 3 | 10.0 | 74.8 | 2.3 | 10.3 |
|  | 204 | 21 | 4 | 12.7 | 78.7 | 0.3 | 12.7 |
|  | 146 | 44 | 5 | 11.7 | 81.0 | 10.4 | 12.9 |
|  | 136 | 68 | 6 | 11.5 | 81.8 | 10.0 | 12.7 |
|  |  | 2–3 days | C[b] | 11.6 | 81.4 | 9.4 | 12.7 |
|  | 136 | 93 | 7 | 11.3 | 82.6 | 10.8 | 12.5 |
|  |  | 4–5 days | C-1[b] | 11.0 | 81.8 | 11.0 | 12.2 |
|  | 142 | 165 | 8 | 10.4 | 83.0 | 11.4 | 11.5 |
|  | 142 | 189 | 9 | 10.2 | 83.4 | 10.5 | 11.2 |
|  | 146 | 213 | 10 | 9.7 | 80.2 | 11.2 | 10.7 |
|  | 139 | 238 | 11 | 9.6 | 83.4 | 11.1 | 10.7 |
|  | 143 | 261 | 12 | 9.9 | 81.9 | 11.0 | 11.0 |
|  | 133 | 333 | 13 | 9.2 | 83.4 | 11.3 | 10.3 |
|  | 138 | 356 | 14 | 8.9 | 83.5 | 11.1 | 9.9 |
|  | 138 | 381 | 15 | 8.8 | 83.0 | 11.3 | 9.8 |
|  | 131 | 405 | 16 | 8.7 | 82.8 | 11.2 | 9.7 |

[a]Corrected for benzene in effluent sample
[b]Composite product

TABLE 6

| Column Temp (°C.) | Pressure DIFF (psi) | Pressure EXIT (psi) | Pot Temp. (°C.) | Time (hr) | Sample (#) | Alkylate Conc. (%) | 2-Phenyl Sel. (%) | $C_6H_6$ Conc. (%) |
|---|---|---|---|---|---|---|---|---|
| 149–129 | 0.1 | 0 | 188 | 4 | 1 | 3.8 | | 6.3 |
| 152–126 | 0 | 0 | 200 | 20 | 2 | 1.8 | | 32.7 |
| 195–108 | 0 | 0 | 199 | 25 | 3 | 5.7 | | 8.7 |
| 218–111 | 0 | 0 | 201 | 28 | 4 | 0.8 | | 67.5 |
| 212–118 | 0 | 0 | 201 | 44 | 5 | 8.8 | 71.7 | 4.5 |
| 209–114 | 0.2 | 0 | 198 | 52 | 6 | 2.4 | | 47.3 |
| 228–116 | 0 | 0 | 197 | 68 | 7 | 6.9 | 72.6 | 12.4 |
| 187–107 | 0.5 | 0 | 197 | 76 | 8 | 2.9 | 74.6 | 44.1 |
| | | | | 76 | 9ᵃ | 4.8 | 72.9 | 25.3 |
| | | | | | 9Cᵇ | 6.8 | 72.2 | 1.0 |
| 174–107 | 0 | 0 | 178 | 6 | 10 | 4.1 | 79.2 | 54.9 |
| 170–106 | 0 | 0 | 172 | 22 | 11 | 2.0 | | 59.8 |
| | | | | 28 | 12ᵃ | 6.6 | 76.8 | 26.8 |
| 142–107 | 0 | 0 | 136 | 31 | 13 | 4.8 | 67.9 | 18.9 |
| 141–110 | 0 | 0 | 138 | 47 | 14 | 4.4 | 65.9 | 16.9 |
| 142–110 | 0 | 0 | 136 | 55 | 15 | 5.0 | 63.9 | 16.6 |
| 168–111 | 0 | 0 | 131 | 71 | 16 | 4.1 | 64.8 | 16.7 |
| 170–108 | 0 | 0 | 150 | 79 | 17 | 5.0 | 72.0 | 8.8 |
| 175–113 | 0 | 0 | 143 | 95 | 18 | 5.9 | 68.1 | 15.2 |
| 145–106 | 0 | 5.2 | 188 | 14 | 19 | 3.2 | 60.2 | 9.0 |
| 149–108 | 0 | 4.2 | 186 | 20 | 20 | 4.8 | 66.3 | 12.0 |
| 160–118 | 0 | 11.7 | 213 | 29 | 21 | 4.2 | | 6.7 |
| 160–119 | 0 | 9.3 | 210 | 44 | 22 | 5.2 | | 6.6 |

ᵃComposite product
ᵇStripped composite product

EXAMPLES 6–8

These examples illustrate the preparation of linear alkyl benzene using hydrogen fluoride-modified mordenite catalysts with different fluoride treatment levels.

Following the procedures of Example 1, the alkylation unit was charged with benzene (100 ml), a 10 g sample of hydrogen fluoride-modified mordenite prepared by the procedure of Example B, plus a mix of benzene (50 ml) and 1-decene (10 g). Three HF-treated mordenites were tested, having the composition:

Catalyst "C" 0.25% HF on mordenite (CBV-20A)

Catalyst "D" 0.50% HF on mordenite (CBV-20A)

Catalyst "E" 1.0% HF on mordenite (CBV-20A)

In each experiment samples of the bottoms liquid fraction were withdrawn at regular periods and subject to gas chromatography analyses. The results are summarized in Table 7.

TABLE 7

| CATALYST | TIME (min) | % LLAB | % ISOS | % HVY | %2 Ph | %3 Ph | %4 Ph | %5 Ph | %6&7 Ph |
|---|---|---|---|---|---|---|---|---|---|
| D | 10 | 11.75 | 0.14 | 0 | 73.36 | 21.87 | 2.89 | 0.94 | 1.02 |
| | 20 | 12.43 | 0.21 | 0 | 72.97 | 21.96 | 3.14 | 1.13 | 0.81 |
| | 30 | 12.88 | 0.21 | 0 | 72.67 | 22.13 | 3.03 | 1.16 | 1.01 |
| | 40 | 12.27 | 0.22 | 0 | 73.02 | 21.92 | 2.85 | 1.06 | 1.14 |
| | 50 | 12.15 | 0.98 | 0 | 72.46 | 21.67 | 3.21 | 1.17 | 1.49 |
| | 50 | 12.24 | 1.01 | 0 | 72.53 | 21.63 | 3.23 | 1.12 | 1.44 |
| | 60 | 12.28 | 0.21 | 0 | 72.96 | 22.07 | 2.93 | 1.14 | 0.91 |
| | 60 | 11.98 | 0.21 | 0 | 72.97 | 22.21 | 2.93 | 1.17 | 0.83 |
| C | 10 | 12.2 | 0.18 | 0 | 72.54 | 22.46 | 3.21 | 0.98 | 0.82 |
| | 20 | 12.7 | 0.39 | 0 | 71.51 | 22.61 | 2.91 | 1.02 | 2.13 |
| | 30 | 12.52 | 0.21 | 0 | 71.96 | 22.68 | 2.96 | 1.04 | 1.36 |
| | 40 | 12.75 | 0.21 | 0 | 71.84 | 22.67 | 3.22 | 1.02 | 1.25 |
| | 50 | 12.98 | 0.21 | 0 | 71.57 | 22.81 | 3.16 | 1.08 | 1.39 |
| | 60 | 12.54 | 0.21 | 0 | 71.45 | 22.81 | 3.19 | 1.12 | 1.44 |
| | 60 | 12.33 | 0.21 | 0 | 71.61 | 22.87 | 2.92 | 1.05 | 1.31 |
| E | 10 | 10.56 | 0.05 | 0 | 75.19 | 19.41 | 2.18 | 3.22 | |
| | 20 | 12.95 | 0.15 | 0 | 74.36 | 19.23 | 3.01 | 3.4 | |
| | 30 | 13.44 | 0.18 | 0 | 74.11 | 19.42 | 3.2 | 3.27 | |
| | 40 | 13.16 | 0.15 | 0 | 074.16 | 19.38 | 3.12 | 3.34 | |
| | 50 | 13.1 | 0.15 | 0 | 74.43 | 19.16 | 3.21 | 3.28 | |
| | 60 | 12.83 | 0.15 | 0 | 74.28 | 19.49 | 2.88 | 3.35 | |
| | 60 | 12.87 | 0.16 | 0 | 73.82 | 19.97 | 2.8 | 3.2 | |

EXAMPLE 9

This example illustrates the inactivity of a heavily loaded hydrogen-fluoride modified mordenite catalyst.

Following the procedures of Example 2, the alkylation unit was charged with 100 cc of a hydrogen fluoride-treated mordenite (CBV-20A) prepared by the method of Example B but having a much higher loading of HF (fluoride content 4.8%). The acidity of said HF-treated mordenite was 0.15 meq/g.

No significant amount of alkylated product was detected by gas chromatography.

EXAMPLE 10

This example illustrates the further alkylation of the crude product of example 4 using a fluorided montmorillonite clay catalyst in a batch mode.

To a three-necked, glass flask fitted with a Dean-Stark trap, condenser, thermometer, and addition funnel, was added 10 g of dried, 0.5% fluorided montmorillonite clay granules having a surface area of about 500 m$^2$/g (20/60 mesh) and 80 ml of benzene. The mixture was heated to reflux and about 25 ml of benzene was collected in the Dean-Stark arm. About 100 g of crude benzene alkylate from Example 4, Table 5, having a bromine number of 1.44, was added to the flask over a period of about 10 minutes and the mix heated to reflux for about 3 hours. The reaction mix was then cooled, filtered to remove the granular catalyst, and flashed to remove excess benzene.

The remaining colorless liquid had a bromine number of 0.10.

GLC analyses of this sample showed:
Total alkylate conc.: 15.34%
2-phenyl isomer content: 77.64%

EXAMPLE 11

This example illustrates the further alkylation of a stripped sample of alkylate from Example 4 using a fluorided montmorillonite clay catalyst in a batch mode.

Using the equipment and following the procedures of Example 10, 20 g of dried 0.5% fluorided montmorillonite clay granules (20/60 mesh) and 80 ml of benzene were placed in the three necked flask, the mix heated to reflux and about 25 ml of benzene was collected in the trap. A 100 g sample of crude benzene alkylate from Example 4, Table 5, that had been stripped to remove both the residual benzene and most of the $C_{10}$–$C_{14}$ paraffin, having a bromine number of 0.31, was then added to the flask and the mix heated to reflux for two hours. The reaction mix was cooled, filtered to remove the granular catalyst, and flashed to remove excess benzene.

The remaining slightly yellow liquid had a bromine number of 0.005.

GLC analyses of this sample showed:
Total alkylate conc.: 97.35%
2-phenyl isomer content: 78.03%

EXAMPLE 12

This example illustrates the further alkylation of the crude product of Example 4 using a fluorided montrnorillonite clay catalyst in a plug-flow reactor system.

To a 100 cc capacity, upflow, stainless-steel, continuous reactor fitted with temperature, pressure, and flow controls was charged 100 cc of 0.5% fluorided montmorillonite clay granules (20/60 mesh) that had previously been dried in a stream of air at 200° C. A 1:1 volume mixture of crude benzene alkylate having a bromine number of about 0.4 from Example 4, Table 5, plus benzene, was charged to said unit at a rate of 100 cc/hr and alkylation conditions were set at 100° C. and 300 psi. Under steady state conditions, samples of product effluent were collected, stripped of excess benzene, and the residual liquid analyzed.

Typical product liquid had a bromine number of 0.02.

GLC analysis of the sample showed:
Total alkylate conc.: 13.2%
2-phenyl isomer content: 75.8% A further stripping of the product liquid at higher temperatures, under vacuum, to remove unreacted $C_{10}$–$C_{14}$ paraffin, yielded a residual liquid showing:
Total alkylate conc.: 97.9%
2-phenyl isomer context: 76.4%

What is claimed is:

1. A process useful for the production of monoalkylated benzene, comprising:
   contacting benzene with an olefin of from about 5 to about 30 carbons in the presence of fluorine-containing mordenite under conditions such that monoalkylated benzene is formed, and (b) contacting the effluent from step (a) with benzene in the presence of a fluorine-containing clay catalyst such that the product of step (b) has a bromine number less than the bromine number of the product of step (a).

2. The process of claim 1, wherein the fluorine-containing mordenite has a silica to alumina molar ratio in a range from about 10:1 to about 50:1, wherein the mordenite has been treated by contacting mordenite with an aqueous hydrogen fluoride solution, wherein the hydrogen fluoride in the aqueous solution has a -concentration in the range from about 0.1 to about 5 percent by weight.

3. The process of claim 1, wherein the olefin has from about 10 to about 14 carbons.

4. The process of claim 1, wherein the monoalkylated benzene contains about 70 or more percent of 2-phenyl isomer.

5. The process of claim 1, wherein the mordenite contains in a range from about 0.1 to about 4 percent by weight of fluorine.

6. The process of claim 1, wherein the clay catalyst is made of montmorillonite clay.

7. The process of claim 1, wherein the clay catalyst has a fluorine content of from about 0.1 percent to about 10 percent by weight.

8. The process of claim 1, wherein the bromine number of the product of step (b) is less than about 0.1.

9. The process of claim 1, wherein step (2) is conducted in a continuous manner.

10. A process useful for the production of monoalkylated benzene, comprising:
   introducing a feed comprising olefin having about 5 to about 30 carbons and benzene into fluorine-containing mordenite catalyst bed under conditions such that monoalkylated benzene is produced;
   collecting benzene, olefin, and monoalkylated benzene that descends from the catalyst bed in a reboiler;
   heating the contents of the reboiler such that benzene refluxes to further contact the fluorine-containing mordenite;
   removing monoalkylated benzene having a bromine number from the reboiler;
   contacting the monoalkylated benzene removed from the reboiler with benzene in the presence of a fluorine-containing clay catalyst such that the bromine number of the monoalkylated benzene removed from the reboiler is reduced.

11. The process of claim 10, wherein the fluorine-containings mordenite has a silica to alumina molar ratio of from about 10:1 to about 50:1, wherein the mordenite has been treated by contacting (a) mordenite with an aqueous hydrogen fluoride solution, wherein the hydrogen fluoride in the aqueous solution has a concentration of about 0.1 to about 5 percent by weight.

12. The process of claim 10, wherein the olefin has from about 10 to about 14 carbons.

13. The process of claim 10, wherein the monoalkylated benzene contains about 70 or more percent of 2-phenyl isomer after contacting with the clay.

14. The process of claim 10, wherein the benzene to olefin ratio in the feed is about 2:1 to about 20:1, wherein the catalyst bed is maintained at a temperature of about 75° C. to about 200° C., and wherein the feed is introduced into the catalyst bed at a liquid hourly space velocity of about 0.1 $hr^{-1}$.

15. The process of claim 10, further comprising collecting water overhead of the mordenite catalyst bed in a water trap.

16. The process of claim 10, wherein the mordenite contains in a range from about 0.1 to about 4 percent by weight of fluorine.

17. The process of claim 10, wherein the clay catalyst is made of montmorillonite clay.

18. The process of claim 10, wherein the clay catalyst has a fluorine content of from about 0.1 percent to about 4 percent by weight.

19. The process of claim 10, wherein the clay catalyst has been calcined in the temperature range of 100° C. to 600° C.

20. The process of claim 10, wherein the clay catalyst has a surface area of greater than 30 $m^2/g$.

21. The process of claim 10, wherein the bromine number is reduced to less than about 0.1.

22. The process of claim 10, wherein the contacting is conducted in a continuous manner.

* * * * *